United States Patent [19]

Schaefer

[11] 4,399,073

[45] Aug. 16, 1983

[54] PREPARATION OF TERTIARY ALKYL ISOCYANATES

[75] Inventor: Frederic C. Schaefer, Darien, Conn.

[73] Assignee: American Cyanamid Company, Stamford, Conn.

[21] Appl. No.: 371,913

[22] Filed: Apr. 26, 1982

[51] Int. Cl.$^3$ .......................................... C07C 118/00
[52] U.S. Cl. ........................ 260/453 P; 260/453 AR
[58] Field of Search ..................................... 260/453 P

[56] References Cited

U.S. PATENT DOCUMENTS 4,130,577  12/1978  Nagato et al. ................... 260/453 P
4,224,238  9/1980  Nagato et al. ................... 260/453 P

*Primary Examiner*—Dolph H. Torrence
*Attorney, Agent, or Firm*—Steven J. Hultquist

[57] ABSTRACT

A process for the production of tertiary alkyl isocyanates, such as tetramethylxylylene diisocyanate, is disclosed in which the corresponding tertiary alkyl halide is reacted with an alkali metal cyanate in the presence of water in an amount between 0.02 and 0.2 percent based on the weight of the reaction mixture.

13 Claims, No Drawings

PREPARATION OF TERTIARY ALKYL ISOCYANATES

This invention relates to tertiary alkyl isocyanates and in particular provides a method for producing mono- and poly-isocyanates by reaction of the corresponding tertiary alkyl halides with alkali metal cyanates.

This invention has general applicability to the preparation of alkyl isocyanates in which the isocyanato group is attached to a tertiary carbon atom and in particular isocyanates in which the tertiary alkyl carbon atom is a substituent on an aromatic nucleus. The invention has particular applicability to the preparation of isocyanates, such as tetramethylxylylene diisocyanates, and is illustrated in that context below, but is equally applicable to the preparation of a variety of isocyanates such as tertiary butyl isocyanate, dipentene diisocyanate and tri-(isocyanatoisopropyl)benzenes.

This invention specifically relates to production of tertiary alkyl isocyanates by the reaction of the corresponding tertiary alkyl halide with an alkali metal cyanate, such as is described in U.S. Pat. Nos. 4,130,577 and 4,224,238. These patents describe the preparation of a wide variety of tertiary alkyl isocyanates by such reaction in an aprotic organic solvent and in the presence of a catalyst selected from the mineral acid salts and carboxylic acid salts of zinc, iron, antimony, tin and cobalt. The catalyst can also desirably include promoters, such as tertiary amines and preferably pyridine.

It has heretofore been believed that in the reaction of alkali metal cyanates with tertiary alkyl halides the reaction mixture had to be substantially anhydrous, as it was known that amounts of water in excess of 0.5% by weight had a deleterious effect on the yields of desired isocyanates. Undesirable side reactions, such as hydrolysis of the starting halide, were believed to take place in the presence of water.

It has now been found that in fact the reaction of alkyl halides with alkali metal cyanates is impeded under substantially anhydrous conditions. Thus in accordance with the present invention it has been found that substantially improved yields of the desired isocyanates are obtained when water is present in the reaction mixture in a very small amount, between 0.02% and 0.2% based on the weight of the entire reaction mixture.

Except for the addition of water to the reaction mixture to maintain the amount of water within the stated range, the reaction of alkyl halide and alkali metal cyanate proceeds generally as described in the above noted patents.

Thus in accordance with this invention, as indicated above, the alkyl halide utilized can be any alkyl halide in which the halogen is bonded to a tertiary carbon atom. The reaction is generally selective, and the same or similar functional groups, such as halides, attached to secondary or primary carbon atoms are non-reactive under the conditions of the reaction. Poly tertiary alkyl halides can be reacted to produce the corresponding polyisocyanates.

The alkali metal cyanate can be any alkali metal cyanate, but preferably is sodium cyanate. The proportions of halide to cyanate are generally stoichiometric or with a slight excess of cyanate and range between ratios of 1:0.8 to about 1:4, preferably in the range of 1:1–1:2, of equivalents of halide to moles of cyanate.

The reaction is carried out preferably in an aprotic organic solvent which is non-reactive with hydrogen halides and forms neither salts nor adducts with hydrogen halides. The solvents which can be used are those known in the art for this reaction. Particularly suitable are halogenated aliphatic and aromatic hydrocarbons, methylene dichloride being preferred.

Generally the reaction is carried out between 0° C. and 100° C. for a sufficient period of time to convert the tertiary alkyl halide substantially to the corresponding tertiary alkyl isocyanate. In some circumstances higher temperatures may be used. Tertiary halides are usually unstable over 50° C., however, and dehydrochlorination can occur at higher temperatures. The solvent can also limit the temperature. Methylene dichloride, for example boils at 40° C. Normally the reactions are carried out at atmospheric pressure.

Generally catalysts effective to promote the reaction of a tertiary alkyl halide with an alkali metal cyanate ae are metal salts of mineral acids and various carboxylic acids, particularly salts of metals such as zinc, iron, antimony, tin and cobalt. Zinc chloride has been found a particularly effective catalyst and is prefereed with alkyl halide reactants, such as cumylchloride and di(-chloroisopropyl)benzenes. As is known in the art, only small amounts of catalyst are required, and preferably the amount is just that sufficient to obtain the desired reaction. Usually 0.5 to about 50 mole percent of catalyst, and preferably about 1 to 10 mole percent of catalyst, based on the starting tertiary alkyl halide, is utilized.

Preferably the catalyst is employed in conjunction with promoters, such as amines, particularly tertiary amines. Pyridine is the preferred promoter. The amount of promoter is based on the amount of catalyst employed and preferably is from 0.5 to 2.0 moles per mole of catalyst. The amount of promoter should not exceed 2 moles per mole of catalyst.

Preferably when zinc chloride and pyridine are employed as catalyst and promoter, respectively, the zinc chloride and pyridine are first complexed and then reacted with the alkali metal cyanate all prior to reaction with the alkyl halide, as described in my co-pending application. It is believed that the active catalytic agency is $Zn(Pyridine)_2(NCO)_2$ Preparation of the complex prior to reaction with alkyl halide greatly improves yields.

EXAMPLES

A stock solution of zinc chloride-pyridine complex was prepared by adding 10.6 ml (0.03 mole) of pyridine to a slurry of anhydrous zinc chloride (9.10 g, 0.067 mole) in 250 ml of methylene dichloride (containing 30 ppm $H_2O$). The solid dissolved essentially completely as the mixture was stirred for several minutes. The solution then was made up to 350 cc with additional methylene dichloride.

35 ml. aliquots of this stock solution of catalyst were taken and to each was added 16.9 grams of oven-dried technical NaOCN (0.22 mole, 0.02% $H_2O$). Water in varying amounts was added to all but the first aliquot. In each case the mixture was stirred for 20 minutes at room temperature. A solution of 23.1 g of p-TMXDC ($\alpha,\alpha,\alpha',\alpha'$-tetramethyl-p-xylylene dichloride, 0.10 mole) in 45 ml. of methylene dichloride was then added to each aliquot and stirring continued in each case. At intervals the reaction mixture was analyzed by gas chromatography with the results shown in Table I which also indicates the weight percent of water present in each aliquot, including that initially present in the methylene dichloride and sodium cyanate, as well as that added to each of the last four aliquots. In Table I the first aliquot, which was substantially anhydrous and to which no water was added, is designated Example A. The remaining four aliquots to which water was added are designated Examples 1, 2, 3, and 4.

EXAMPLE 6

α,α,-Dimethyl-3-Isopropenylbenzene Isocyanate m-TMI

This compound was prepared in the same manner as described with reference to p-TMI in Example 5, above, starting with 1,3-diisopropenylbenzene. Comparable yields were obtained; B.P. 118° C. at 5 mm Hg.

TABLE 1

| Example No. | Water Added, Ml. | Total Water Content, % by weight | Reaction Temp, °C. | Reaction Time | Reaction Mixture Composition, % | | | |
|---|---|---|---|---|---|---|---|---|
| | | | | | DIPEB | TMI | HI | TMXDI |
| A | 0 | 0.0044* | 30° | 3 hrs | 29.2 | 44.8 | 0 | 25.5 |
| 1 | 0.07 | 0.055 | 30° | 65 min | 11.6 | 30.7 | 1.5 | 55.8 |
| | | | | 4 hr | 2.4 | 14.7 | 3.8 | 78.6 |
| 2 | 0.14 | 0.11 | 30° | 60 min | 0.3 | 7.6 | 5.0 | 84.7 |
| | | | | 120 min | 0.3 | 7.1 | 5.0 | 86.4 |
| 3 | 0.14 | 0.11 | 25° | 90 min | 0.5 | 6.3 | 4.8 | 86.7 |
| 4 | 0.21 | 0.165 | 30° | 30 min | 0.6 | 6.7 | 10.1 | 81.4 |

*—Substantially anhydrous
DIPEB = unreacted p-di (2-chloroisopropyl) benzene measured by gas chromotography as p-diisopropenyl benzene
TMI = p-isopropenyl-α,α-dimethylbenzyl isocyanate probably partly present in reaction mixture as the mono-chloride.
HI = p-(1-hydroxy-1-methylethyl)-α,αdimethylbenzyl isocyanate
TMXDI = p-α,α,α'α'-tetramethyl-p-xylylene diisocyanate Examples 1-4 show in comparison with Example A the superior yields which are surprisingly obtained when water is added to the reaction mixture in amounts in the range of 0.02 to 0.20% by weight.

EXAMPLE 5

α,α-Dimethyl-4-Isopropenylbenzyl Isocyanate (p-TMI)

1067 g (6.7 mole) of p-diisopropenyl benzene was dissolved in three liters of methylene dichloride and treated at 0° C. with 6.7 mole of dry, gaseous hydrogen chloride. The resulting crude solution contained α,α, dimethyl-4-isopropenylbenzyl chloride as a predominant organic product.

A catalyst solution was prepared by stirring a mixture of 64.4 g zinc chloride, 75 g of pyridine and 1580 ml of methylene dichloride (0.002% H₂O) until an essentially clear solution was obtained (30 minutes). An additional 1800 ml of methylene dichloride and 1065 g (14.7 moles) of 90% sodium cyanate (0.5% H₂O) were then added, and the suspension was stirred for 15 minutes.

The chloride reagent solution prepared above was then gradually added over 10 minutes to the catalyst solution, and the reaction mixture was held at 20°-25° with gentle cooling. The total water content of the reaction mixture at that point was 0.06% by weight.

After a 2 hour reaction period no further change was found to be occurring as determined by gas chromotography, and the reaction products, so determined, were present in molar ratios of approximately 17:74:3 of diisopropenyl benzene:p-TMI:p:TMXDI.

The solvent was then distilled from the reaction mixture, and the residue was extracted with 3 liters of hexane. This extract was concentrated to recover 1448 g of crude p-TMI containing 4.06 mole (60.6% yield) of p-TMI. The crude p-TMI was then purified by flash distillation through a wiped film evaporator to remove polymeric by-products and residual zinc catalyst, and thereafter was fractionally distilled through a packed column; B.P. 121° C. at 5 mm Hg.

EXAMPLE 7

1,3,5-Tris(1-Isocyanato-1-Methylethyl)Benzene

A catalyst solution was prepared by stirring a mixture of zinc chloride (1.0 moles), pyridine (2.0 mole) and methylene dichloride until the solid dissolved. 1.42 moles of 90% sodium cyanate containing 0.5% H₂O were added to 100 ml. of the solution so prepared which contained the equivalent of 24 m.moles of Zn(pyr)₂Cl₂. The mixture was stirred for an hour, and thereafter 0.33 mole of 1,3,5-tris(1-chloro-1-methylethyl)benzene dissolved in 530 ml methylene chloride was added. At this point the reaction mixture contained 0.05% water by weight.

After stirring overnight at room temperature gas chromatographic analysis indicated 81% conversion to triisocyanate had been achieved. The solvent was evaporated, and the product was recrystallized from hexane giving a 59% yield; M.P. 65.5°-66.5° C.

EXAMPLE 8

2,6-Bis(1-Isocyanato-1-Methylethyl)Naphthalene 2,6-Bis(1-chloro-1-methylethyl)naphthalene (0.178 mole) was prepared by passing a stream of dry gasous hydrogen chloride through a methylene dichloride suspension of 2,6-diisopropenylnaphthalene (37.2 g, 0.18 mole) which had previously been cooled to 4° C. After conversion of the diisopropenylnaphthalene to the dichloride the solvent was removed in vacuo at 30° C. leaving an off-white solid. The solid was redissolved in 250 ml of methylene dichloride, cooled to 4° C. and slowly added to a cooled (4° C.) methylene dichloride suspension of sodium cyanate/zinc chloride catalyst solution. The catalyst solution had previously been prepared by vigorously stirring a suspension of zinc chloride (2.0 g, 0.014 mole), pyridine (2.46 g, 0.03 mole), anhydrous, 90% sodium cyanate (34 g, 0.47 mole) and 0.25 ml of water in 300 ml methylene dichloride for 2 hours at ambient temperature. After all the dichloride solution had been added the reaction mixture contained 0.03% by weight of water.

The reaction mixture was allowed to stand at 4° C. for two hours and then was allowed to warm to ambient temperature and stirred an additional 18 hours. Magnesium sulfate and Hyflo (a proprietary filtration aid) were then added. After 5 minutes the solution was filtered to remove solids. The solvent was then removed in vacuo leaving 57 g of an oily solid. The oily solid was mixed with 600 ml, of hexane heated at 70° C. for one hour, filtered through Hyflo and then cooled to ambient temperature. The solid which crystallized was collected and air dried, affording 25 g (first crop) of product. The mother liquor was then concentrated and cooled affording a second crop of 12 g. The final product, 37 g (70% yield), was found to have a chloride level of 370 ppm and an isocyanate content equivalent to 6.66 meq/g. (melting range 85.5°–87° C.).

EXAMPLE 9

α,α-Dimethylbenzylisocyanate

α,α-Dimethylbenzylchloride was prepared by passing a stream of dry halogen chloride gas through a solution of methylene dichloride (750 ml) and α-methylstyrene (500 g, 4.2 moles) at 4° C. The reaction and work-up were the same as employed for the preparation of 2,6-Bis(1-isocyanato-1-methylethyl)naphthalene described in Example 8. The resulting monochloride was dissolved in 750 ml. methylene dichloride and was added to a cooled (4° C.) catalyst solution previously prepared from anhydrous, 90% sodium cyanate (389 g, 5.39 moles), pyridine (50 ml, 0.633 mole), zinc chloride (39.15 g, 0.28 mole) and 1 ml H$_2$O in 1075 ml. methylene dichloride. At this point the reaction mixture contained 0.04% by weight of water.

After the reaction mixture had been stirred at ambient temperature for 3 days magnesium sulfate and Hyflo were added and the solution filtered to remove solids. Solvent was then removed in vacuo leaving an oil which was found to be 66% dimethylbenzylisocyanate and 33% α-methylstyrene. The isocyanate was further purified by fractional distillation affording 275 g (45%) of α,α-dimethylbenzylisocyanate.

I claim:

1. In a process for production of a tertiary alkyl isocyanate by reacting the corresponding tertiary alkyl halide with an alkali metal cyanate in a ratio between 1:0.8 and 1:4 of equivalents of halide to moles of cyanate at a temperature of between 0° C. and 100° C. in a reaction mixture further comprising an aprotic organic solvent and an amount of catalyst effective to promote the reactiion of said alkyl halide and said alkali metal cyanate, the improvement in which said reaction mixture further comprises water in an amount of 0.02% to 0.0.2% based on the weight of said reaction mixture.

2. The improvement according to claim 1 in which said alkyl halide is a di(2-chloroisopropyl)benzene.

3. The improvement according to claim 1 in which said alkyl halide is a α,α-dimethylisopropenylbenzyl chloride.

4. The improvement according to claim 1 in which said alkyl halide is 1,3,5-tri(1-chloro-1-methylethyl)benzene.

5. The improvement according to claim 1 in which said alkyl halide is a di(1-chloro-1-methylethyl)naphthalene.

6. The improvement according to claim 1 in which said alkyl halide is α,α-dimethylbenzyl chloride.

7. The improvement according to any of claims 1–6 in which said solvent is methylene dichloride.

8. The improvement according to any of claims 1–6 in which said catalyst is zinc chloride.

9. The improvement according to any of claims 1–6 in which said catalyst further includes a promoter.

10. The improvement according to claim 9 in which said promoter is pyridine.

11. The improvement according to any of claims 1–6 in which the proportion of water present in said reaction mixture is about 0.11% based on the total weight of the reaction mixture.

12. In a process for production of a tertiary alkyl isocyanate by reacting the corresponding tertiary alkyl halide with an alkali metal cyanate in a ratio between 1:0.8 and 1:4 of equivalents of halide to moles of cyanate at a temperature of between 0° C. and 100° C. in a reaction mixture further comprising an aprotic organic solvent and an amount of catalyst effective to promote the reaction of said alkyl halide and said alkyli metal cyanate, the improvement which comprises adding water to said reaction mixture in an amount of 0.02% to 0.0.2% based on the weight of said reaction mixture.

13. In a process for production of a tertiary alkyl isocyanate by reacting the corresponding tertiary alkyl halide with an alkali metal cyanate in a ratio between 1:0.8 and 1:4 of equivalents of halide to moles of cyanate at a temperature of between 0° C. and 100° C. in a reaction mixture further comprising an aprotic organic solvent and an amount of catalyst effective to promote the reaction of said alkyl halide and said alkali metal cyanate, the improvement which comprises adjusting the amount of water in said reaction mixture to between 0.02% and 0.0.2% based on the weight of said reaction mixture.

* * * * *